United States Patent [19]

Aoki et al.

[11] Patent Number: 4,524,132

[45] Date of Patent: Jun. 18, 1985

[54] COLOR PHOTOGRAPHIC SILVER HALIDE LIGHT-SENSITIVE MATERIAL

[75] Inventors: Kozo Aoki; Makoto Umemoto; Akira Ogawa, all of Kanagawa, Japan

[73] Assignee: Fuji Photo Film Co., Ltd., Kanagawa, Japan

[21] Appl. No.: 647,953

[22] Filed: Sep. 6, 1984

[30] Foreign Application Priority Data

Sep. 6, 1983 [JP] Japan ................................ 58-163979

[51] Int. Cl.$^3$ ................................................ G03C 7/26

[52] U.S. Cl. .................................... 430/552; 430/553; 430/554; 430/555; 430/556; 430/557; 430/558

[58] Field of Search ............... 430/505, 552, 553, 554, 430/555, 556, 557, 558

[56] References Cited

U.S. PATENT DOCUMENTS

| | | | |
|---|---|---|---|
| 3,591,383 | 7/1971 | Yoshida et al. | 430/553 |
| 3,880,661 | 4/1975 | Lau et al. | 430/553 |
| 3,891,445 | 6/1975 | Arai et al. | 430/555 |
| 4,333,999 | 6/1982 | Lau | 430/552 |
| 4,362,810 | 12/1982 | Usagawa et al. | 430/553 |
| 4,368,257 | 1/1983 | Usagawa et al. | 430/558 |

*Primary Examiner*—J. Travis Brown

*Attorney, Agent, or Firm*—Sughrue, Mion, Zinn, Macpeak, and Seas

[57] ABSTRACT

A color photographic silver halide light-sensitive material is described, comprising a support base having thereon a silver halide emulsion layer wherein said material contains at least one coupler represented by formula (I)

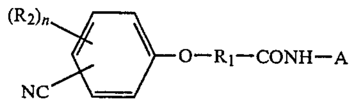

(I)

wherein A represents a yellow coupler residue, a magenta coupler residue, or a cyan coupler residue; $R_1$ represents a substituted or unsubstituted acyclic or cyclic alkylene group; $R_2$ represents a halogen atom, a hydroxyl group, a cyano group, a substituted or unsubstituted alkyl group, a substituted or unsubstituted acylamino group, a substituted or unsubstituted sulfonamido group or a substituted or unsubstituted acyl group; and n represents an integer of 0 to 3.

18 Claims, No Drawings

COLOR PHOTOGRAPHIC SILVER HALIDE LIGHT-SENSITIVE MATERIAL

FIELD OF THE INVENTION

This invention relates to a color photographic silver halide light-sensitive material containing novel cyan dye-forming couplers.

BACKGROUND OF THE INVENTION

When a color photographic silver halide light-sensitive material (hereinafter also sometimes referred to simply as a light-sensitive material) is exposed to light and then color-developed, an oxidized aromatic primary amine developing agent reacts with a dye-forming coupler to form a color image. In this method, color reproduction is usually achieved by the subtractive color process; that is, for reproduction of blue, green, and red, dyes of yellow, magenta, and cyan in complementary relation to blue, green, and red, respectively, are formed.

The couplers used in the above-described light-sensitive materials are dissolved in a high boiling point organic solvent or an alkaline aqueous solution and then dispersed in a photographic emulsion. In general, the former method, i.e., the oil droplet dispersion method, has an advantage of various excellent performances. Therefore, the couplers are required to be highly soluble in the high boiling organic solvents and excellent in dispersibility and stability in the photographic emulsion. In addition, it is demanded that the couplers show high color developing properties, such as maximum color density and dye-forming rate, and afford, upon development processing, a color image excellent in heat- and light-fastness, spectral absorption characteristics, and transparency.

Further, in view of the recent demand for minimizing environmental pollution, it is desired to use a color developer containing no benzyl alcohol while retaining the dye-forming properties of the couplers attained by using a color developer containing benzyl alcohol.

Such couplers that satisfy all of the above-described requirements have not yet been developed and an improvement has been long desired.

Phenols and naphthols are widely used as cyan dye-forming couplers. Conventional phenols and naphthols, however, have a disadvantage in that color images derived therefrom are inferior in storage stability. For example, color images derived from a 2-acylaminophenol cyan coupler described in U.S. Pat. Nos. 2,367,531, 3,369,929, 2,423,730 and 2,801,171 are generally inferior in heat-fastness. Color images derived from a 2,5-diacylaminophenol cyan coupler described in U.S. Pat. Nos. 2,772,162 and 2,895,826 are generally inferior in light-fastness. A 1-hydroxy-2-naphthamide cyan coupler can provide only color images which are generally inferior in both light-fastness and heat-fastness. Besides, these conventional couplers exhibit poor dye-forming properties in a color developer containing no benzyl alcohol.

The magenta dye-forming couplers include pyrazolone type compounds, pyrazolobenzimidazole type compounds, indazolone type compounds, pyrazolotriazole type compounds and pyrazoloimidazole type compounds. However, these couplers have various disadvantages. For example, a pyrazolone type magenta coupler disclosed in U.S. Pat. Nos. 2,369,489 and 2,600,788 has good dye-forming properties but shows insufficient dye-forming properties in a color developer containing no benzyl alcohol, and additionally the color density changes due to formalin, etc. The magenta couplers described in Japanese Patent Application (OPI) (Open to Public Inspection) No. 117034/74 are greatly dependent for dye-forming properties on the presence of benzyl alcohol, although some of them do provide color images excellent in light-fastness.

Compounds having an open-chain active methylene group are generally used as yellow dye-forming couplers. Conventionally known yellow couplers, e.g., those described in U.S. Pat. Nos. 3,408,194 and 3,644,498, provide color images having high light-fastness but their dye-forming properties greatly depend on benzyl alcohol. The couplers disclosed in Japanese Patent Application (OPI) No. 87650/75 exhibit stable dye-forming properties against pH changes of a color developer, but their dye-forming properties are greatly dependent on the presence of benzyl alcohol.

SUMMARY OF THE INVENTION

Accordingly, an object of this invention is to provide a color photographic silver halide light-sensitive material containing cyan dye-forming couplers which can eliminate the aforesaid disadvantages and are superior in various performances.

Another object of this invention is to provide a coupler which exhibits high dye-forming properties, i.e., a maximum color density and a dye-forming rate, in color developers, particularly sufficiently high dye-forming properties, even in developers containing no benzyl alcohol.

A further object of this invention is to provide a coupler having high solubility in high boiling organic solvents and providing a color image excellent in transparency and spectral absorption characteristics.

These and other objects of the present invention can be accomplished by the couplers represented by formula (I)

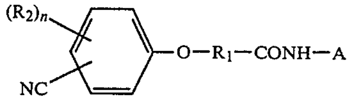

(I)

wherein A represents a yellow coupler residue (e.g., a residue of an open-chain active methylene type yellow coupler, etc.), a magenta coupler residue (e.g., a residue of a 5-pyrazolone type, pyrazolinobenzimidazole type, indazolone type, pyrazolotriazole type or cyanoacetyl type coupler, etc.) or a cyan coupler residue (e.g., a residue of a phenol type, naphthol type or 5-hydroxyquinoline type coupler, etc.); $R_1$ represents an acyclic or cyclic alkylene group (e.g., a methylene group, a propylene group, a propylidene group, a tridecylidene group, a cyclohexylidene group, etc.) or a acyclic or cyclic alkylene group which is substituted by a substituent such as an alkyl group, an aryl group, a heterocyclic group, an alkoxy group (e.g., a methoxy group, a 2-methoxyethoxy group, etc.), an aryloxy group (e.g., a phenoxy group, a 2,4-di-t-amylphenoxy group, a 2-chlorophenoxy group, etc.), a carboxyl group, a carbonyl group (e.g., an acetyl group, a benzoyl group, etc.), an ester group (e.g., a methoxycarbonyl group, a phenoxycarbonyl group, an acetoxy group, a toluenesulfonyloxy group, etc.), an amido group (e.g., an acetylamino group, an ethylcarbamoyl group, a dimethylcarbamoyl group, a methanesulfonamido group, a butylsulfamoyl group, etc.), a sulfamido group (e.g., a dipropylsulfamoylamino group, etc.), an imido group (e.g., a succinimido group, a hydantoinyl group, etc.), a ureido group (e.g., a phenylureido group, a dimethylureido group, etc.), a sulfonyl group (e.g., a methanesulfonyl group, etc.), a hydroxyl group, a cyano group, a nitro group, a halogen atom, a thio group (e.g., an ethylthio group, a phenylthio group, etc.) and the like; $R_2$ represents a halogen atom, a hydroxyl group, a cyano group, a substituted or unsubstituted alkyl group (e.g., a methyl group, a butyl group, a dodecyl group, etc.), a substituted or unsubstituted acylamino group (e.g., an acetylamino group, a benzoylamino group, etc.), a substituted or unsubstituted sulfonamido group (e.g., a butylsulfonamido group, a benzenesulfonamido group, etc.) or a substituted or unsubstituted acyl group (e.g., an acetyl group, a benzoyl group, etc.), wherein the substituents are the same as those enumerated for the substituted groups as represented by $R_1$; and n represents an integer of from 0 to 3.

DETAILED DESCRIPTION OF THE INVENTION

In formula (I), $R_1$ preferably has from 1 to 22 carbon atoms.

A is preferably bonded to the amido group at a position of A other than the coupling position thereof. The yellow coupler residue represented by A preferably includes a residue derived from formula (II)

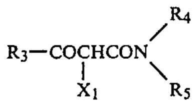

(II)

wherein $R_3$, $R_4$, and $R_5$ each represents a group used in usual 4-equivalent type acylacetanilide couplers or malondianilide couplers. Specific examples for $R_3$ typically include an alkyl group (e.g., a methyl group, an isopropyl group, a t-butyl group, etc.), an aryl group (e.g., a phenyl group, a naphthyl group, etc.), a heterocyclic group (e.g., a pyridyl group, a thiazolyl group, an oxazolyl group, etc.), an alkenyl group (e.g., a 1,1-dimethyl-3-butylenyl group, etc.) and a group represented by the formula

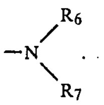

$R_4$, $R_5$, $R_6$, and $R_7$, which may be the same or different from each other, each typically represents a hydrogen atom, an alkyl group, an aryl group, or a heterocyclic group as defined for $R_3$. $R_3$, $R_4$, $R_5$, $R_6$, and $R_7$ further include the same groups as enumerated above that can be substituted by the same substituents as described for $R_1$. $X_1$ represents a group which is releasable upon the oxidative coupling reaction with a developing agent. Specific examples for $X_1$ include a hydrogen atom, a halogen atom, an alkoxy group, an aryloxy group, an acyloxy group, an alkylthio group, an arylthio group, a sulfonyloxy group, an alkyl- or aryloxycarbonyloxy group, a carbamoylamino group, an imido group, an azo group, a sulfo group, a thiocyanato group and the like. These groups as represented by $X_1$ may contain a photographically useful group. It is preferable that at least one group bonding to A in the formula (I) is bonded to any of $R_3$, $R_4$, $R_5$, $R_6$, $R_7$, and $X_1$.

The magenta coupler residue as represented by A in formula (I) preferably includes residues derived from compounds represented by formula (III), (IV), (V), (VI), or (XV) as described below.

Formula (III) is

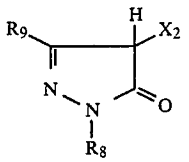

(III)

wherein $R_8$ and $R_9$ each represents a group used in usual 4-equivalent type pyrazolone couplers; and $X_2$ represents a group releasable upon an oxidative coupling reaction with a developing agent.

In the above formula (III), specific examples of $R_8$ are a substituted or unsubstituted acyclic or cyclic alkyl group (e.g., a methyl group, a t-butyl group, a dodecyl group, etc.), a substituted or unsubstituted alkenyl group (e.g., an allyl group, etc.), a substituted or unsubstituted aryl group (e.g., a phenyl group, a naphthyl group, etc.) and a substituted or unsubstituted heterocyclic group (e.g., a pyridyl group, a quinolyl group, etc.), wherein the substituents are the same as those enumerated for $R_1$. Specific examples of $R_9$ include an anilino group, an acylamino group and a ureido group. Specific examples of $X_2$ are the same as those enumerated for $X_1$. It is preferable that at least one group bonding to A in the formula (I) is bonded to any of $R_8$, $R_9$ or $X_2$, or is substituted in the formula (III) as $R_9$.

Formula (IV) is

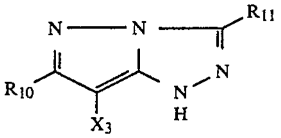

(IV)

wherein $R_{10}$ and $R_{11}$ each represents a hydrogen atom, a substituted or unsubstituted acyclic or cyclic alkyl group (e.g., a methyl group, a t-butyl group, a dodecyl group, etc.), a substituted or unsubstituted alkenyl group (e.g., an allyl group, etc.), a substituted or unsubstituted aryl group (e.g., a phenyl group, a naphthyl group), a substituted or unsubstituted heterocyclic group (e.g., a pyridyl group, a quinolyl group, a thiazolyl group, etc.), a substituted or unsubstituted amino group, a substituted or unsubstituted acylamino group, a hydroxyl group, a substituted or unsubstituted alkoxy group, a substituted or unsubstituted aryloxy group, a substituted or unsubstituted alkoxycarbonyl group, a substituted or unsubstituted aryloxycarbonyl group, a substituted or unsubstituted carbamoyl group, a substituted or unsubstituted sulfamoyl group or a substituted or unsubstituted sulfonamido group, wherein the substituents are the same as those enumerated for $R_1$; and $X_3$ represents a group which can be released upon an oxidative coupling reaction with a developing agent as specifically enumerated for $X_1$. It is preferred that at least one group bonding to A in the formula (I) is bonded to any of $R_{10}$, $R_{11}$ or $X_3$, or is substituted in the formula (IV) as $R_{10}$ or $R_{11}$.

Formula (V) is

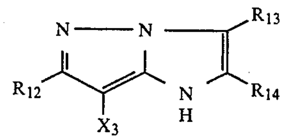

(V)

wherein $R_{12}$, $R_{13}$, and $R_{14}$ each represents a hydrogen atom, an acyclic or cyclic alkyl group, an aryl group, a heterocyclic group, a cyano group, an alkoxy group, an aryloxy group, an acylamino group, an anilino group, a ureido group, a sulfamoyl group, a sulfonamido group, a carbamoyl group, a sulfonyl group, or an alkoxycarbonyl group; and $X_3$ is as defined above; or $R_{13}$ and $R_{14}$ jointly form a 5- to 7-membered ring. It is preferred that at least one group bonding to A in the formula (I) is bonded to any of $R_{12}$, $R_{13}$, $R_{14}$ or $X_3$, or is substituted in the formula (V) as $R_{12}$, $R_{13}$, or $R_{14}$.

Formula (VI) is

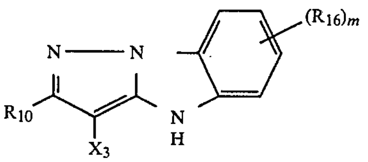

(VI)

wherein $R_{10}$ and $X_3$ are as defined above for formula (IV); $R_{16}$ represents a hydrogen atom, a substituted or unsubstituted acyclic or cyclic alkyl group, a substituted or unsubstituted alkenyl group, a substituted or unsubstituted aralkyl group, a substituted or unsubstituted aryl group, a substituted or unsubstituted heterocyclic group, a halogen atom, a substituted or unsubstituted alkoxy group, a substituted or unsubstituted aryloxy group, a cyano group, a substituted or unsubstituted acylamino group, a substituted or unsubstituted sulfonamido group, a substituted or unsubstituted carbamoyl group, a substituted or unsubstituted sulfamoyl group, a substituted or unsubstituted alkoxycarbonyl group, or a substituted or unsubstituted sulfamoylamino group, wherein the substituents are the same as those enumerated for $R_1$; and m represents 0 or an integer of 1 to 4. It is preferred that at least one group bonding to A in the formula (I) is bonded to any of $R_{10}$, $R_{16}$ or $X_3$, or is substituted in the formula (VI) as $R_{10}$ or $R_{16}$.

Formula (XV) is

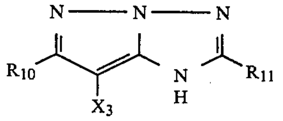

(XV)

wherein $R_{10}$, $R_{11}$ and $X_3$ are as defined above for formula (IV).

The cyan coupler residue as represented by A in the formula (I) preferably includes residues derived from compounds represented by formula (VII)

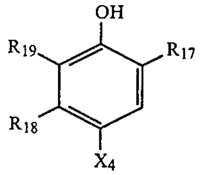

(VII)

wherein $R_{17}$ and $R_{18}$ each represents a hydrogen atom, an acyclic or cyclic alkyl group (e.g., a methyl group, a tetradecyl group, a cyclohexyl group, etc.), an alkoxy group (e.g., a methoxy group, an isopropoxy group, a hexadecyloxy group, etc.), an aryloxy group (e.g., a phenoxy group) or a group represented by the formula (VIII), (IX), (X), (XI), or (XII):

$$-NHCO-B \qquad (VIII)$$

$$-NH-SO_2-B \qquad (IX)$$

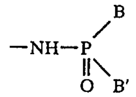

(X)

$$-NHCONH-B \qquad (XI)$$

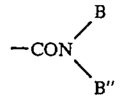

(XII)

wherein B and B′, which may be the same or different, each represents an acyclic or cyclic alkyl group, an aryl group, or a heterocyclic group; B″ represents a hydrogen atom, a substituted or unsubstituted acyclic or cyclic alkyl group, a substituted or unsubstituted aryl group or a substituted or unsubstituted heterocyclic group, wherein the substituents are the same as those enumerated for $R_1$; $R_{19}$ represents a hydrogen atom, an acyclic or cyclic alkyl group, an aryl group, a heterocyclic group, a halogen atom, an alkoxy group or an aryloxy group; or $R_{18}$ and $R_{19}$ jointly form a 5- or 6-membered non-metallic atom ring; and $X_4$ is a group releasable upon an oxidative coupling reaction with a developing agent as specifically enumerated for $X_1$. It is preferable that a least one group bonding to A in the formula (I) is bonded to any of $R_{17}$, $R_{18}$, $R_{19}$ or $X_4$, or is substituted as $R_{17}$ or $R_{18}$.

In formula (I), it is preferable that the group —CN and the group —O—$R_1$—CONH—A are in the relation of an ortho-position or para-position.

Preferred examples for $R_2$ include a halogen atom, an alkyl group, an acylamino group, and a sulfonamido group.

It is preferable that n is 0.

A in the formula (I) is preferably a cyan coupler residue represented by formula (VII). More preferably, formula (I) is represented by the formula (XIII) or (XIV).

(XIII)

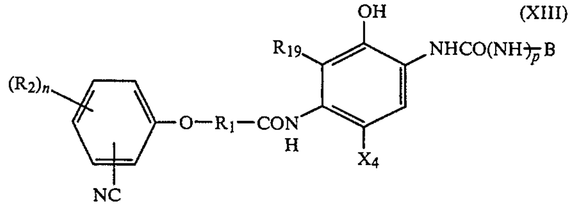

-continued

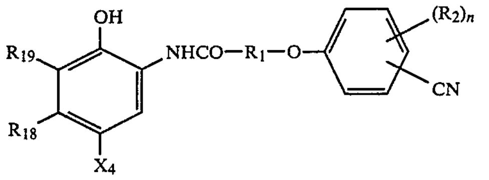

(XIV)

wherein $R_1$, $R_2$, n, $X_4$, $R_{18}$, $R_{19}$ and B are as defined above; and p is 0 or 1.

In formula (XIII), $R_{19}$ is preferably a hydrogen atom.

In formula (XIV), $R_{19}$ preferably represents a hydrogen atom or a non-metallic atomic group to form a 5- or 6-membered ring, more preferably containing at least one nitrogen atom, together with $R_{18}$.

In formula (XIII), B is preferably an aryl group and p is preferably 0.

Typical examples of the couplers of the present invention are shown below, although the present invention is not limited thereto.

Y-1

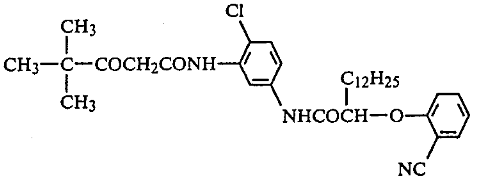

Y-2

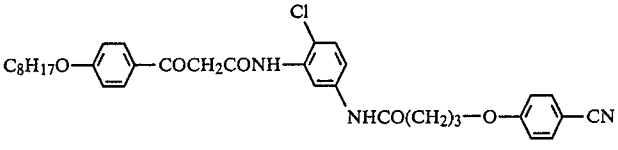

Y-3

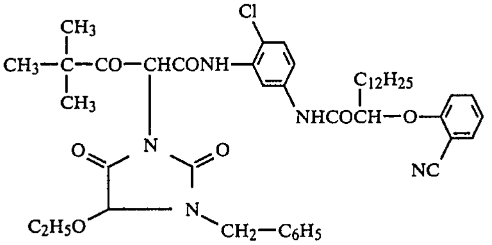

Y-4

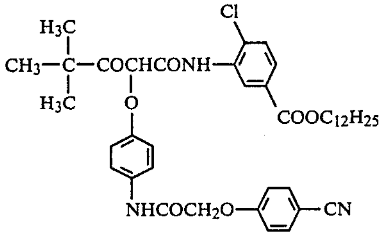

Y-5

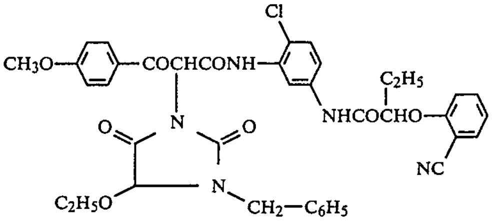

M-1

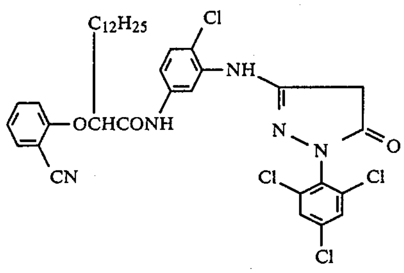

M-2

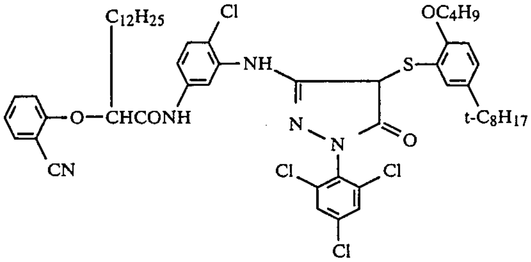

M-3

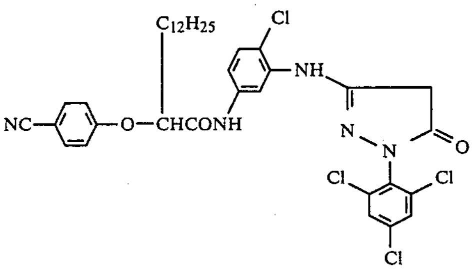

-continued
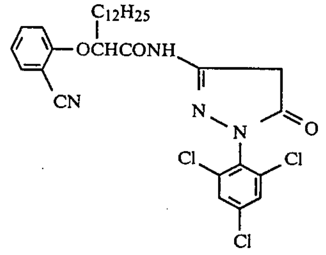
M-4
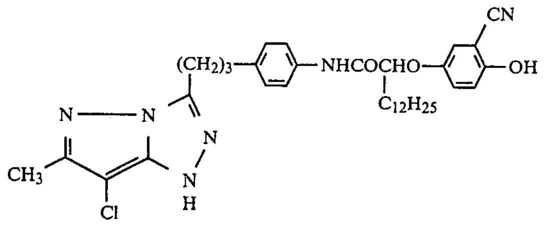
M-5
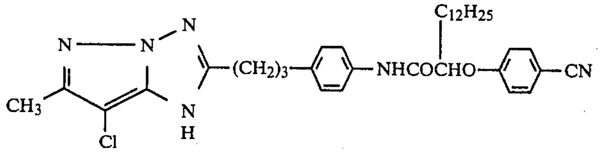
M-6
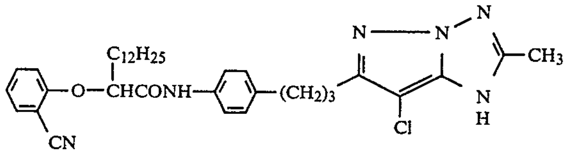
M-7
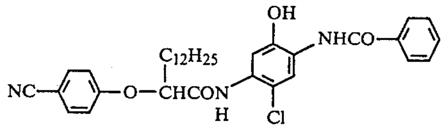
C-1
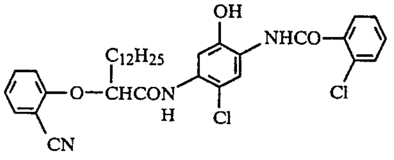
C-2
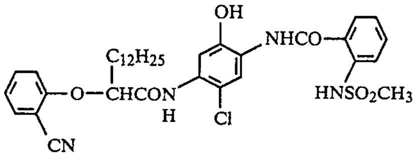
C-3
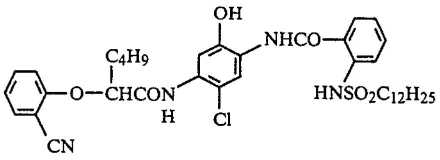
C-4
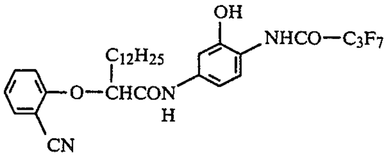
C-5
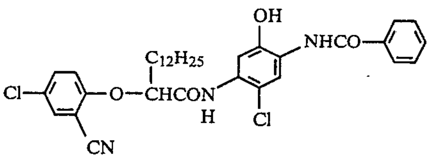
C-6
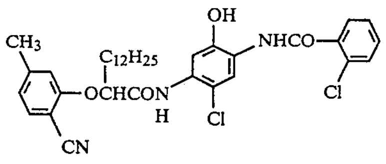
C-7
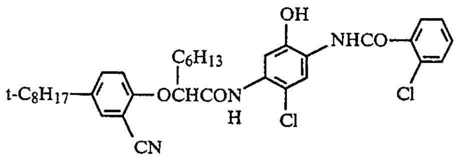
C-8
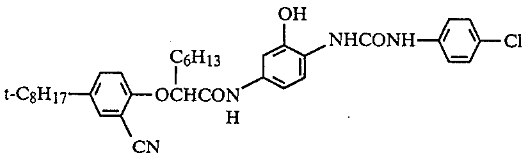
C-9

-continued

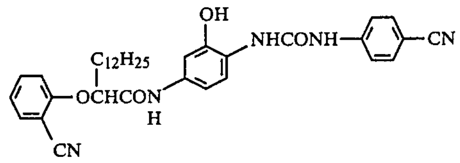

C-10

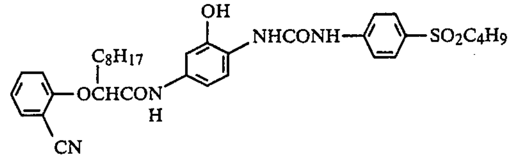

C-11

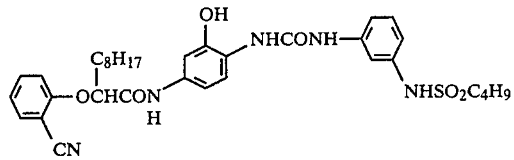

C-12

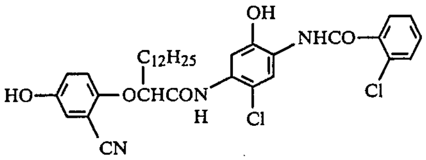

C-13

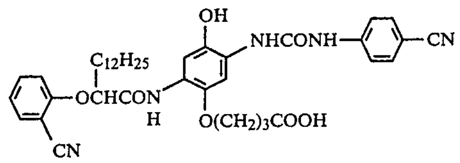

C-14

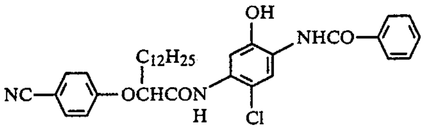

C-15

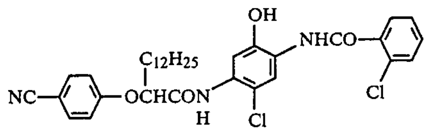

C-16

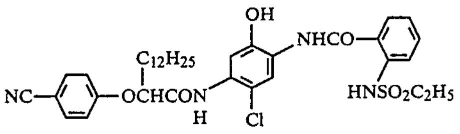

C-17

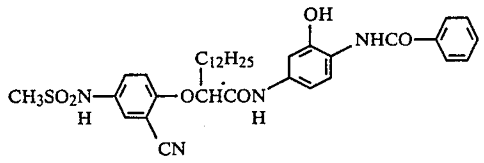

C-18

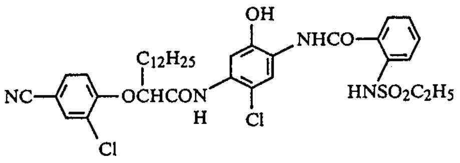

C-19

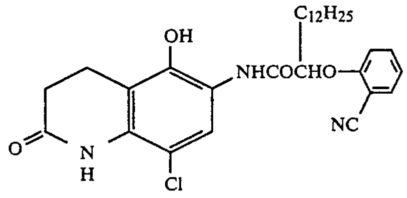

C-20

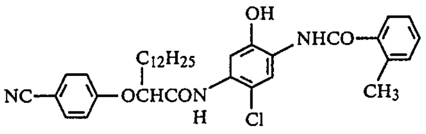

C-21

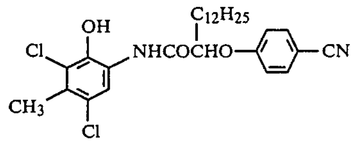

C-22

The couplers according to the present invention can generally be synthesized by the following process.

A phenol having a cyano group which corresponds to the formula (I) is reacted with a halocarboxylic acid or an ester thereof containing the $R_1$ moiety under basic conditions (e.g., caused by potassium hydroxide, potassium carbonate, etc.). In the case of using the ester, the product is then hydrolyzed with an alkali and treated with thionyl chloride, etc., to form an acid chloride. The reaction product thus obtained is then reacted with an amino compound corresponding to A—$NH_2$, which is a coupler nucleus, to obtain the desired coupler.

Typical preparation examples are shown below.

1. Synthesis of o-Cyanophenoxytetradecanoyl Chloride

To a mixture of 119 g of o-cyanophenol, 340 g of ethyl 2-bromotetradecanoate and 150 g of potassium carbonate was added 300 ml of dimethylformamide, and the mixture was heated on a steam bath for 2 hours while stirring. After cooling, the reaction mixture was poured into ethyl acetate and extracted, followed by washing with water. The solvent was removed by distillation under reduced pressure, and the residue was dissolved in 500 ml of ethanol. A solution of 60 g of sodium hydroxide in 150 ml of water was added thereto. Three hours later, the mixture was poured into water and made acidic with hydrochloric acid. The thus-formed precipitate was collected to obtain 301 g of crystals. After drying, 300 ml of benzene and then 104 ml of thionyl chloride were added to the crystals, and the mixture was refluxed for 2 hours, followed by concentration under reduced pressure, to obtain 333 g of the desired compound as a pale brown oily substance.

2. Synthesis of Coupler M-1

To a mixture of 300 ml of acetonitrile and 60 ml of ethyl acetate was added 40.4 g of 3-(5-amino-2-chloroanilino)-1-(2,4,6-trichlorophenyl)pyrrolin-5-one, and 38.1 g of the acid chloride obtained in Synthesis 1 above was added dropwise thereto under heat-refluxing. After refluxing for 3 hours, the reaction mixture was cooled, and ethyl acetate was added thereto. The mixture was repeatedly washed with water, dried, and subjected to distillation to remove the solvent. The residue was crystallized from acetonitrile containing a small amount of ethyl acetate to obtain 58.5 g of the desired Coupler M-1.

Elementary Analysis: Calculated (%): C 59.10, H 5.37, N 9.58. Found (%): C 58.91, H 5.22, N 9.67.

3. Synthesis of Coupler C-1

In the same manner as described in Synthesis 1, but using p-cyanophenol in place of o-cyanophenol, p-cyanophenoxytetradecanoyl chloride was obtained as a pale brown oily substance.

To 200 ml of acetonitrile was added 26.3 g of 5-amino-2-benzoylamino-4-chlorophenol, and 36.9 g of the above-prepared acid chloride was added dropwise thereto under heat-refluxing. The reaction mixture was refluxed for 2 hours, followed by cooling. The precipitated crystals were collected and recrystallized from acetonitrile to obtain 50.1 g of the desired Coupler C-1.

Melting Point: 127°-129° C.

Elementary Analysis: Calculated (%): C 69.19, H 6.83, N 7.12. Found (%): C 69.23, H 6.78, N 7.04.

Other couplers can be synthesized in the same manner as described above.

Photographic emulsions prepared according to the present invention may contain other dye-forming couplers in addition to the couplers of the present invention.

These couplers are preferably nondiffusing and contain a hydrophobic group called a ballast group in the molecule. They may be either 4-equivalent or 2-equivalent relative to silver ions. The photographic emulsions may further contain colored couplers having the effect of color correction or the so-called DIR couplers which release a development inhibitor with development. The couplers may be those providing colorless coupling reaction products.

As yellow couplers, known open-chain ketomethylene-based couplers can be used. Of these, benzoylacetanilide- and pivaloylacetanilide-based compounds are advantageous. Specific examples of yellow couplers which can be used are described in, for example, U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, and Japanese Patent Application (OPI) Nos. 26133/72, 73147/73, 102636/76, 6341/75, 123342/75, 130442/75, 21827/76, 87650/75, 82424/77 and 115219/77.

Magenta couplers which can be used include pyrazolone-based compounds, indazolone-based compounds, cyanoacetyl compounds and the like, with the pyrazolone-based compounds being particularly advantageous. In addition, pyrazolotriazole-based compounds, pyrazoloimidazole-based compounds and pyrazolopyrazole-based compounds may also be used. Specific examples of the magenta couplers which can be used are described, for example, in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication No. 6031/65, and Japanese Patent Application (OPI) Nos. 20826/76, 58922/77, 129538/74, 74027/74, 159336/75, 42121/77, 74028/74, 60233/75, 26541/76 and 55122/78.

Cyan couplers which can be used include phenol-based compounds, naphthol-based compounds, and the like. Specific examples of useful cyan couplers are described, for example, in U.S. Pat. Nos. 2,369,929, 2,434,272, 2,474,293, 2,521,908, 2,895,826, 3,304,892, 3,311,476, 3,458,315, 3,476,563, 3,583,971, 3,591,383, 3,767,411 and 4,004,929, West German Patent Application (OLS) Nos. 2,414,830 and 2,454,329, and Japanese Patent Application (OPI) Nos. 59838/73, 26034/76, 5055/73, 146828/76, 69624/77 and 90932/77.

Specific examples of the colored couplers which can be used are described, for example, in U.S. Pat. Nos. 3,476,560, 2,521,908 and 3,034,892, Japanese Patent Publication Nos. 2016/69, 22335/63, 11304/67 (corresponding to U.S. Pat. No. 3,481,741) and 32461/69 (corresponding to U.S. Pat. No. 3,583,971), Japanese Patent Application (OPI) Nos. 26034/76 (corresponding to U.S. Pat. No. 4,138,258) and 42121/77, and West German Patent Application (OLS) No. 2,418,959.

Specific examples of the DIR couplers which can be used are described, for example, in U.S. Pat. Nos. 3,227,554, 3,617,291, 3,701,783, 3,790,384 and 3,632,345, West German Patent Application (OLS) Nos. 2,414,006, 2,454,301 and 2,454,329, British Pat. No. 953,454, Japanese Patent Application (OPI) Nos. 69624/77 and 122335/74, and Japanese Patent Publication No. 16141/76.

In addition to DIR couplers, the light-sensitive materials may further contain compounds releasing a development inhibitor with development. Specific examples of such compounds are described, for example, in U.S. Pat. Nos. 3,297,445 and 3,379,529, West German Patent Application (OLS) No. 2,417,914, and Japanese Patent Application (OPI) Nos. 15271/77 and 9116/78.

Two or more of the couplers of the present invention can be incorporated in the same layer of a light-sensitive material. Further, the same compound can be incorporated in two or more layers. Also, the coupler of this invention can be added to a non-light-sensitive layer in addition to the light-sensitive silver halide layer.

When the coupler is added to the silver halide light-sensitive layer, the couplers of the present invention are usually used in an amount of from $1\times10^{-3}$ to $7\times10^{-1}$ mol, and preferably from $1\times10^{-2}$ to $5\times10^{-1}$ mol, per mol of silver contained in the emulsion layer. When the couplers of the present invention are used in combination with the above-described other couplers, it is preferable that the total amount of the couplers forming the same color falls within the above range.

The above-described couplers can be introduced in silver halide emulsion layers by known methods, such as the method disclosed in U.S. Pat. No. 2,322,027. For example, the couplers are dissolved in phthalic acid alkyl esters (e.g., dibutyl phthalate, dioctyl phthalate, etc.), phosphoric esters (e.g., diphenyl phosphate, triphenyl phosphate, tricresyl phosphate, dioctylbutyl phosphate, etc.), citric esters (e.g., tributyl acetylcitrate, etc.), benzoic esters (e.g., octyl benzoate, etc.), alkylamides (e.g., diethyllaurylamide, etc.), fatty acid esters (e.g., dibutoxyethyl succinate, dioctyl azelate, etc.), or organic solvents having a boiling point ranging from about 30° C. to about 150° C., such as lower alkyl acetates (e.g., ethyl acetate, butyl acetate, etc.), ethyl propionate, sec-butyl alcohol, methyl isobutyl ketone, β-ethoxyethyl acetate and methyl cellosolve acetate, and then dispersed in hydrophilic colloids. The above-described high boiling and low boiling organic solvents may be used in combination with each other.

Furthermore, the dispersion process using polymeric compounds as disclosed in Japanese Patent Publication No. 39853/76 and Japanese Patent Application (OPI) No. 59943/76 can also be used.

When the couplers contain acid groups, such as a carboxyl group and a sulfo group, they can be introduced in the hydrophilic colloids in the form of alkaline aqueous solutions.

The light-sensitive materials of the present invention may contain ultraviolet absorbers in the hydrophilic colloid layer thereof. The ultraviolet absorbers which can be used include benzotriazole compounds substituted by an aryl group (e.g., those described in U.S. Pat. No. 3,533,794), 4-thiazolidone compounds (e.g., those described in U.S. Pat. Nos. 3,314,794 and 3,352,681), benzophenone compounds (e.g., those described in Japanese Patent Application (OPI) No. 2784/71), cinnamic esters (e.g., those described in U.S. Pat. Nos. 3,705,805 and 3,707,375), butadiene compounds (e.g., those described in U.S. Pat. No. 4,045,229) and benzoxazole compounds (e.g., those described in U.S. Pat. No. 3,700,455). In addition, the compounds described in U.S. Pat. No. 3,499,762 and Japanese Patent Application (OPI) No. 48535/79 can also be used. Further, ultraviolet-absorbing couplers (e.g., α-naphthol-based cyan dye-forming couplers), ultraviolet-absorbing polymers, etc., may be used. These ultraviolet absorbers may be mordanted to a specific layer.

Photographic emulsions which can be used in the present invention can be prepared according to the methods as described, for example, in P. Glafkides, *Chimie et Physique Photographique,* Paul Montel (1967), G. F. Duffin, *Photographic Emulsion Chemistry,* The Focal Press (1966) and V. L. Zelikman et al., *Making and Coating Photographic Emulsion,* The Focal Press (1964).

In the present invention, silver halide emulsions having a regular crystal form and a nearly uniform particle size may be employed.

Two or more silver halide emulsions separately prepared can be used as an admixture thereof.

The couplers of this invention can be used in combination with an emulsion containing plate-shaped particles, preferably particles having a diameter/thickness ratio of not less than 5/1, and more preferably not less than 8/1, in an amount of 50% or more based on the total projection surface.

During formation of the silver halide grains or physical ripening thereof, cadmium salts, zinc salts, lead salts, thallium salts, iridium salts or complex salts thereof, rhodium salts or complex salts thereof, iron salts or complex salts thereof, etc., may be present in combination in the system.

It is advantageous to use gelatin as a binder for photographic emulsions or protective colloids, but other hydrophilic colloids may be employed.

For the purpose of preventing fogging of the light-sensitive materials during production, storage or photographic processing or stabilizing photographic performances of the light-sensitive materials, the photographic emulsions used in the present invention can contain various compounds known as antifoggants or stabilizers, such as azoles, e.g., benzothiazolium salts, nitroindazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (particularly, 1-phenyl-5-mercaptotetrazole), etc.; mercaptopyrimidines; mercaptotriazines; thioketo compounds, e.g., oxazolinethione, etc.; azaindenes, e.g., triazaindenes, tetraazaindenes (particularly, 4-hydroxy-substituted (1,3,3a,7)tetraazaindenes), pentaazaindenes, etc.; benzenethiosulfonic acid, benzenesulfinic acid, benzenesulfonic acid amide; and the like. For example, the compounds described in U.S. Pat. Nos. 3,954,474 and 3,982,947 and Japanese Patent Publication No. 28660/77 can be used.

For the purpose of improving sensitivity or contrast, or accelerating development, the emulsion layers of the photographic light-sensitive materials of this invention may contain polyalkylene oxides or their derivatives such as ethers, esters, amines, etc., thioether compounds, thiomorpholines, quaternary ammonium salt compounds, urethane derivatives, urea derivatives, imidazole derivatives, 3-pyrazolidones, and the like.

Photographic emulsion layers used herein may be subjected to spectral sensitization using, for example, methine dyes. Dyes which can be used for spectral sensitization include cyanine dyes, merocyanine dyes, composite cyanine dyes, composite merocyanine dyes, holopolar cyanine dyes, hemicyanine dyes, styryl dyes and hemioxonol dyes. Especially useful are those dyes belonging to cyanine dyes, merocyanine dyes and composite merocyanine dyes. In these dyes, any nuclei which are ordinarily used for cyanine dyes as basic heterocyclic nuclei can be applied. Examples of employable nuclei include a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, and a pyridine nucleus; nuclei resulting from fusion of aliphatic hydrocarbon rings to the above-described nuclei; and nuclei resulting from fusion of aromatic hydrocarbon rings to the above-described nuclei, such as an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus and a quinoline nucleus. These nuclei may be substituted at a carbon atom thereof.

In merocyanine dyes or composite merocyanine dyes, 5- or 6-membered heterocyclic nuclei, such as a pyrazolin-5-one nucleus, a thiohydantoin nucleus, a 2-thiooxazoline-2,4-dione nucleus, a thiazolidine-2,4-dione nucleus, a rhodanine nucleus, a thiobarbituric acid nucleus, etc., can be used as nuclei having a ketomethylene structure.

Specific examples of useful sensitizing dyes are described, for example, in U.S. Pat. Nos. 2,231,658, 2,493,748, 2,503,776, 2,519,001, 2,912,329, 3,656,959, 3,672,897, 3,694,217, 4,025,349 and 4,046,572, German Pat. No. 929,080, British Pat. No. 1,242,588, and Japanese Patent Publication Nos. 14030/69 and 24844/77.

These sensitizing dyes can be used either alone or in combinations of two or more thereof. Such combinations of sensitizing dyes are often used for the purpose of supersensitization. Typical examples of the combined use of sensitizing dyes for supersensitization are given in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, and Japanese Patent Application (OPI) Nos. 110618/77 and 109925/77.

The photographic emulsions may contain, in combination with the above-described sensitizing dyes, dyes or substances which do not exhibit per se a spectral sensitization effect or which do not substantially absorb visible light, but which exhibit a supersensitization effect. Such dyes or substances can include aminostilbene compounds substituted by a nitrogen-containing heterocyclic group as described in U.S. Pat. Nos. 2,933,390 and 3,635,721, aromatic organic acid-formaldehyde condensates as described in U.S. Pat. No. 3,743,510, cadmium salts and azaindene compounds. Especially useful are the combinations described in U.S. Pat. Nos. 3,615,613, 3,615,641, 3,617,295 and 3,635,721.

The light-sensitive materials of the present invention may contain water-soluble dyes in hydrophilic colloidal layers thereof as filter dyes or for various purposes, for example, prevention of irradiation. Such water-soluble dyes include oxonol dyes, hemioxonol dyes, styryl dyes, merocyanine dyes, cyanine dyes and azo dyes, with the oxonol dyes, hemioxonol dyes and merocyanine dyes being particularly useful. Specific examples of the water-soluble dyes are given in British Pat. Nos. 584,609 and 1,177,429, Japanese Patent Application (OPI) Nos. 85130/73, 99620/74, 114420/74 and 108115/77, and U.S. Pat. Nos. 2,274,782, 2,533,472, 2,956,879, 3,148,187, 3,177,078, 3,247,127, 3,540,887, 3,575,704, 3,653,905, 3,718,472, 4,071,312 and 4,070,352.

The light-sensitive materials according to the present invention may contain whiteners, such as stilbene-, triazine-, oxazole- or cumarine-based whiteners, in the photographic emulsion layers or other hydrophilic colloid layers. These whiteners may be water-soluble or insoluble. In the latter case, the whiteners are used in the form of dispersions.

In carrying out the present invention, known anti-fading agents can be used in combination. Further, color image stabilizers as used in this invention may be used individually or in combination of two or more thereof. Known anti-fading agents include hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028, and British Pat. No. 1,363,921; gallic acid derivatives as described in U.S. Pat. Nos. 3,457,079 and 3,069,262; p-alkoxyphenols as described in U.S. Pat. Nos. 2,735,765 and 3,698,909, and Japanese Patent Publication Nos. 20977/74 and 6623/77; o-oxyphenol derivatives as described in U.S. Pat. Nos. 3,432,300, 3,573,050, 3,574,627 and 3,764,337 and Japanese Patent Application (OPI) Nos. 35633/77, 147434/77 and 152225/77; and bisphenols as described in U.S. Pat. No. 3,700,455.

The light-sensitive materials of the present invention may contain anti-color fogging agents, such as hydroquinone derivatives, aminophenol derivatives, gallic acid derivatives, ascorbic acid derivatives and so on. Specific examples of the anti-color-fogging agents are described in U.S. Pat. Nos. 2,360,290, 2,336,327, 2,403,721, 2,418,613, 2,675,314, 2,701,197, 2,704,713, 2,728,659, 2,732,300 and 2,735,765, Japanese Patent Application (OPI) No. 92988/75, and Japanese Patent Publication No. 23813/75.

The present invention can be applied to multilayer polychromatic photographic materials comprising a support having thereon at least two layers showing different spectral sensitivities. Multilayer natural color photographic materials usually comprise a support having thereon at least one red-sensitive emulsion layer, at least one green-sensitive emulsion layer, and at least one blue-sensitive emulsion layer. The order for these layers to be provided may be optionally selected according to the particular intended use. The red-sensitive emulsion layer, green-sensitive emulsion layer and blue-sensitive emulsion layer usually contain a cyan coupler, a magenta coupler and a yellow coupler, respectively, with different combinations being employable in some cases.

Photographic processing of the light-sensitive materials according to the present invention can be carried out by known procedures using known processing solutions. The processing temperature usually ranges from 18° C. to 50° C., but temperatures lower than 18° C. or higher than 50° C. can also be employed.

The color developer is generally an alkaline aqueous solution containing a color developing agent. The color developing agent includes known primary aromatic amine developers, such as phenylenediamines (e.g., 4-amino-N,N-diethylaniline, 3-methyl-4-amino-N,N-diethylaniline, 4-amino-N-ethyl-β-hydroxyethylaniline, 3-methyl-4-amino-n-ethyl-N-β-hydroxyethylaniline, 3-methyl-4-amino-N-ethyl-N-β-methanesulfoamidoethylaniline, 4-amino-3-methyl-N-ethyl-N-β-methoxyethylaniline, etc.). In addition, such compounds as disclosed in L. F. A. Mason, *Photographic Processing Chemistry,* Focal Press, pp. 226 to 229 (1966), U.S. Pat. Nos. 2,193,015 and 2,592,364, and Japanese Patent Application (OPI) No. 64933/73 may also be used.

The color developer can further contain pH buffers, such as sulfites, carbonates, borates, and phosphates of alkali metals, and development inhibitors or antifoggants, such as bromides, iodides and organic antifoggants. If desired, it may contain hard water-softening agents, preservatives (e.g., hydroxylamine), organic solvents (e.g., benzyl alcohol and diethylene glycol), development accelerators (e.g., polyethylene glycol, quaternary ammonium salts and amines), dye-forming couplers, competitive couplers, foggants (e.g., sodium borohydride), auxiliary developing agents (e.g., 1-phenyl-3-pyrazolidone), tackifiers, the polycarboxylic acid-based chelating agents described in U.S. Pat. No. 4,083,723, and the antioxidants described in West German Patent Application (OLS) No. 2,622,950.

After color development, the photographic emulsion layers are usually subjected to bleaching treatment. The bleaching treatment may be performed with a fixing treatment, or the treatments may be performed separately. Bleaching agents which can be used include compounds of multivalent metals, e.g., iron (III), cobalt (III), chromium (VI), copper (II), etc., as well as peracids, quinones, nitroso compounds, and the like. Examples of these bleaching agents include ferricyanides, dichromates, organic complex salts of iron (III) or cobalt (III), such as complex salts of aminopolycarboxylic acids (e.g., ethylenediaminetetraacetic acid, nitrolotriacetic acid, 1,3-diamino-2-propanoltetraacetic acid, etc.) or organic acids (e.g., citric acid, tartaric acid, malic acid, etc.); persulfates, permanganates; and nitrosophenol. Of these, potassium ferricyanide, iron (III) sodium ethylenediaminetetraacetate and iron (III) ammonium ethylenediaminetetraacetate are particularly useful. Ethylenediaminetetraacetic acid/iron (III) complex salts are useful in both an independent bleaching solution and a combined bleaching and fixing bath.

The bleaching or bleach-fixing solutions can contain various additives, such as the bleach accelerators described in U.S. Pat. Nos. 3,042,520 and 3,241,966 and Japanese Patent Publication Nos. 8506/70 and 8836/70, the thiol compounds described in Japanese Patent Application (OPI) No. 65732/78, and the like.

The present invention will now be illustrated in greater detail by reference to the following non-limiting examples.

EXAMPLE 1

A mixture of 3.15 mmol of Coupler Y-3, 10 g of tricresyl phosphate and 20 ml of ethyl acetate was heated at 50° C. to form a solution. The resulting solution was added to 100 ml of an aqueous solution containing 10 g of gelatin and 0.4 g of sodium dodecylbenzenesulfonate, followed by stirring. The resulting mixture was then finely emulsified and suspended by passing through a preheated colloid mill 5 times.

The whole emulsion as prepared above was added to 400 g of a photographic emulsion containing 21 g of silver chlorobromide and 24 g of gelatin, and 30 ml of a 2% aqueous solution of 4,6-dichloro-4-hydroxytriazine was added thereto. The resulting mixture was adjusted to a pH of 6.0 and then uniformly coated on a triacetate fiber film base together with a protective layer. The thus-prepared material was designated as Sample A.

Samples B, C, and D were prepared in the same manner as described above except that Coupler Y-3 was replaced by equal molar amounts of Couplers M-1, C-1, and C-2, respectively.

For comparison, Samples E, F, and G were prepared in the same manner as described above, but using equal molar amounts of Comparative Couplers (101), (102), and (103), respectively, in place of Coupler Y-3.

Comparative Coupler (101)

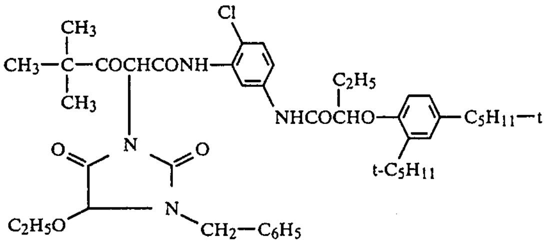

-continued

Comparative Coupler (102)

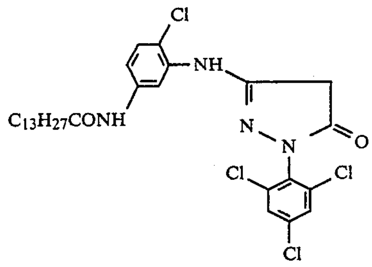

Comparative Coupler (103)

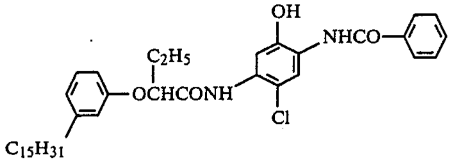

Each film material was continuously exposed to light through a wedge for sensitometry and then processed as follows:

| Color Development Processing (at 33° C.) Step | Time (sec) |
|---|---|
| 1. Color Development | 210 |
| 2. Bleaching and Fixing | 90 |
| 3. Rinsing | 150 |

The treating solution used in each step had the following composition:

| | |
|---|---|
| Color Developer | |
| Benzyl Alcohol | 15.0 ml |
| Diethylene Glycol | 8.0 ml |
| Ethylenediaminetetraacetic Acid | 5.0 g |
| Sodium Sulfite | 2.0 g |
| Anhydrous Potassium Carbonate | 30 g |
| Hydroxylamine Sulfate | 3.0 g |
| Potassium Bromide | 0.6 g |
| 4-Amino-N—ethyl-N—(β-methanesulfonamido-ethyl)-m-toluidine Sesquisulfate Monohydrate | 5.0 g |
| Water to make | 1 liter (pH 10.2) |
| Bleaching-Fixing Solution | |
| Ethylenediaminetetraacetic Acid | 4.0 g |
| Iron (III) Ethylenediaminetetraacetate | 40 g |
| Sodium Sulfite | 5.0 g |
| Sodium Thiosulfate (70%) | 150 ml |
| Water to make | 1 liter |

Each sample thus treated was subjected to measurement of the optical density to light corresponding to the respective hue of the coupler. The results obtained are shown in Table 1.

TABLE 1

| Sample | Coupler | Gamma | Maximum Density |
|---|---|---|---|
| A | Y-3 (Invention) | 2.26 | 2.21 |
| E | (101) (Comparison) | 1.90 | 1.81 |
| B | M-1 (Invention) | 2.71 | 2.87 |
| F | (102) (Comparison) | 2.46 | 2.47 |
| C | C-1 (Invention) | 2.50 | 2.67 |
| D | C-2 (Invention) | 2.46 | 2.55 |

TABLE 1-continued

| Sample | Coupler | Gamma | Maximum Density |
|---|---|---|---|
| G | (103) (Comparison) | 2.12 | 2.21 |

As is apparent from Table 1 above, it can be seen that the couplers according to the present invention have excellent color-forming properties, i.e., high maximum density and high gamma.

The absorption spectrum of the cyan image formed in each of the samples containing the cyan coupler was measured. The results obtained are shown in Table 2.

TABLE 2

| Sample | Coupler | Absorption Maximum (nm) | Half Width of the Short Wave Side (nm) |
|---|---|---|---|
| C | C-1 (Invention) | 638 | 60 |
| D | C-2 (Invention) | 641 | 61 |
| G | (103) (Comparison) | 626 | 63 |

For further comparison, a film sample was also prepared in the same manner as above, but using Comparative Coupler (105) having the following formula which absorbs light of relatively long waves. This comparative sample showed a maximum absorption at 638 nm with a broad half value width of 68 nm of the short wave side.

Comparative Coupler (105)

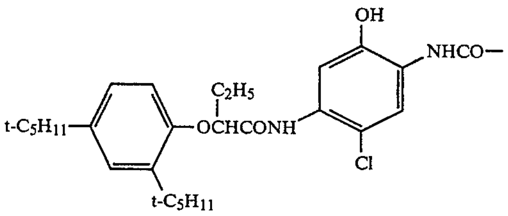

It can be seen from the above results that the couplers of the present invention show an absorption spectrum favorable to color reproduction.

EXAMPLE 2

The first layer (uppermost layer) to the seventh layer (uppermost layer) shown below were coated on a paper support laminated with polyethylene on both sides thereof to prepare a color light-sensitive material. (Sample I)

| | Amount (mg/m$^2$) |
|---|---|
| First Layer (Blue-Sensitive Layer): | |
| Silver Chlorobromide Emulsion (silver bromide: 80 mol %) | 400 (calcd. as Ag) |
| Yellow Coupler$^{(1)}$ | 300 |
| Coupler Solvent$^{(2)}$ | 150 |
| Gelatin | 1,200 |
| Second Layer (Intermediate Layer): | |
| Gelatin | 1,000 |
| Third Layer (Green-Sensitive Layer): | |
| Silver Chlorobromide Emulsion (silver bromide: 70 mol % ) | 300 (calcd. as Ag) |
| Magenta Coupler$^{(3)}$ | 200 |
| Coupler Solvent$^{(4)}$ | 200 |
| Gelatin | 1,000 |
| Fourth Layer (Intermediate Layer): | |
| Ultraviolet Absorber$^{(5)}$ | 600 |

-continued

| | Amount (mg/m$^2$) |
|---|---|
| Ultraviolet Absorber Solvent$^{(6)}$ | 300 |
| Gelatin | 800 |
| Fifth Layer (Red-Sensitive Layer): | |
| Silver Chlorobromide Emulsion (silver bromide: 50 mol %) | 300 (calcd. as Ag) |
| Cyan Coupler$^{(7)}$ | 400 |
| Coupler Solvent$^{(6)}$ | 400 |
| Gelatin | 1,000 |
| Sixth Layer (Ultraviolet Absorbing Layer): | |
| Ultraviolet Absorber$^{(5)}$ | 600 |
| Ultraviolet Absorber Solvent$^{(6)}$ | 300 |
| Gelatin | 800 |
| Seventh Layer (Protective Layer): | |
| Gelatin | 1,000 |

Note:
(1) α-Pivaloyl-α-(2,4-dioxy-5,5'-dimethyl-oxazolidin-3-yl)-2-chloro-5-[α-(2,4-di-tert-pentyloxy)butanamido]acetanilide
(2) Dioctylbutyl Phosphate
(3) 1-(2,4,6-Trichlorophenyl)-3-(2-chloro-5-tetradecanamido)anilino-2-pyrazolon-5-one
(4) Tricresyl Phosphate
(5) 2-(2-Hydroxy-3-sec-butyl-5-tert-butylphenyl)-benzotriazole
(6) Dibutyl Phthalate
(7) 2-[α-(2,4-Di-tert-pentylphenoxy)butanamido]-4,6-dichloro-5-methylphenol Samples J to O were prepared in the same manner as described above but using the couplers shown in Table 3 below in place of the cyan coupler as used for Sample I.

TABLE 3

| Sample | Cyan Coupler | Amount (mg/m$^2$) |
|---|---|---|
| I | (3) | 400 |
| J | C-1 | 480 |
| K | C-2 | 500 |
| L | C-6 | 500 |
| M | C-7 | 520 |
| N | C-1 | 240 |
| | (3) | 200 |
| O | C-2 | 250 |
| | (3) | 200 |

Each sample was exposed to red light through a continuous wedge and then development-processed according to the following steps.

| Step (at 33° C.) | Time (sec) |
|---|---|
| Color Development (A) or (B) | 210 |
| Bleaching-Fixing | 90 |
| Rinsing | 180 |
| Drying | 600 |

The treating solution used in each step had the following composition:

| | |
|---|---|
| Color Developer (A) | |
| Benzyl Alcohol | 15 ml |
| Diethylene Glycol | 5 ml |
| Potassium Carbonate | 25 g |
| Sodium Chloride | 0.1 g |
| Sodium Bromide | 0.5 g |
| Anhydrous Sodium Sulfite | 2 g |
| Hydroxylamine Sulfate | 2 g |
| N—Ethyl-N—β-methanesulfonamidoethyl-3-methyl-4-aminoaniline Sulfate | 4 g |
| Water to make | 1 liter (pH 10 with NaOH) |
| Color Developer (B) | |
| The same composition as Color Developer (A), except containing no benzyl alcohol. | |

-continued

| Bleaching-Fixing Solution | |
|---|---|
| Ammonium Thiosulfate | 124.5 g |
| Sodium Metabisulfite | 13.3 g |
| Anhydrous Sodium Sulfite | 2.7 g |
| Ammonium (Ethylenediaminetetraacetato)-ferrate (III) | 65 g |
| Water to make | 1 liter (pH 6.8) |

After development-processing, the color density of each sample was measured. The results of fog, gamma, and maximum density ($D_{max}$) measurements are shown in Table 4.

TABLE 4

| Sample | Color Developer (A) | | | Color Developer (B) | | | Remark |
|---|---|---|---|---|---|---|---|
| | Fog | Gamma | $D_{max}$ | Fog | Gamma | $D_{max}$ | |
| I | 0.11 | 2.84 | 2.95 | 0.10 | 2.20 | 2.55 | Comparison |
| J | 0.10 | 2.88 | 3.09 | 0.10 | 2.80 | 3.02 | Invention |
| K | 0.11 | 2.83 | 3.06 | 0.11 | 2.74 | 3.03 | Invention |
| L | 0.11 | 2.95 | 2.99 | 0.11 | 2.79 | 2.89 | Invention |
| M | 0.11 | 2.78 | 2.97 | 0.10 | 2.70 | 2.93 | Invention |
| N | 0.11 | 2.85 | 3.06 | 0.11 | 2.65 | 2.81 | Invention |
| O | 0.10 | 2.92 | 3.07 | 0.11 | 2.61 | 2.79 | Invention |

The results shown in Table 4 reveal that Comparative Sample I has markedly reduced color-forming properties in Color Developer (B) containing no benzyl alcohol, whereas all of Samples J to O according to the present invention do not undergo substantial reduction in density and gamma and exhibit sufficient color-forming properties even in the color developer containing no benzyl alcohol.

The reflective absorption spectrum of each of the development-processed Samples I to O was measured, and the results obtained are shown in Table 5.

TABLE 5

| Sample | Absorption Maximum (nm) | Half Width in Short Wave Side (nm) | Absorption at 410 nm |
|---|---|---|---|
| I | 645 | 86 | 0.408 |
| J | 641 | 80 | 0.304 |
| K | 639 | 79 | 0.312 |
| L | 640 | 81 | 0.307 |
| M | 638 | 82 | 0.313 |
| N | 646 | 83 | 0.366 |
| O | 645 | 83 | 0.374 |

It can be seen from Table 5 that all of Samples J to O according to the present invention show narrower half width of absorption, and less side absorption (in the vicinity of 410 nm), when compared with Comparative Sample I, thus indicating that favorable hues are obtained according to the present invention.

While the invention has been described in detail and with reference to specific embodiments thereof, it will be apparent to one skilled in the art that various changes and modifications can be made therein without departing from the spirit and scope thereof.

What is claimed is:

1. A color photographic silver halide light-sensitive material comprising a support base having thereon a silver halide emulsion layer wherein said material contains at least one coupler represented by formula (I)

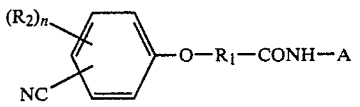

(I)

wherein A represents a yellow coupler residue, a magenta coupler residue, or a cyan coupler residue; $R_1$ represents a substituted or unsubstituted acyclic or cyclic alkylene group; $R_2$ represents a halogen atom, a hydroxyl group, a cyano group, a substituted or unsubstituted alkyl group, a substituted or unsubstituted acylamino group, a substituted or unsubstituted sulfonamido group or a substituted or unsubstituted acyl group; and n represents an integer of 0 to 3.

2. A color photographic silver halide light-sensitive material as in claim 1, wherein said coupler is present in the silver halide emulsion layer.

3. A color photographic silver halide light-sensitive material as in claim 1, wherein the substituent for $R_1$ or $R_2$ is selected from an alkyl group, an aryl group, a heterocyclic group, an alkoxy group, an aryloxy group, a carboxyl group, a carbonyl group, an ester group, an amido group, a sulfonamido group, an imido group, a ureido group, a sulfonyl group, a hydroxyl group, a cyano group, a nitro group, a halogen atom, and a thio group.

4. A color photographic silver halide light-sensitive material as in claim 1, wherein $R_1$ has from 1 to 22 carbon atoms.

5. A color photographic silver halide light-sensitive material as in claim 1, wherein A is bonded to the amido group at a position of A other than a coupling position thereof.

6. A color photographic silver halide light-sensitive material as in claim 1, wherein the yellow coupler residue is derived from formula (II)

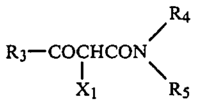

(II)

wherein $R_3$, $R_4$, and $R_5$ each represents a group used in usual 4-equivalent type acylacetanilide couplers or malondianilide couplers; and $X_1$ represents a group releasable upon an oxidative coupling reaction with a developing agent.

7. A color photographic silver halide light-sensitive material as in claim 6, wherein $R_3$ represents a substituted or unsubstituted alkyl group, a substituted or unsubstituted aryl group, a substituted or unsubstituted heterocyclic group, a substituted or unsubstituted alkenyl group, or

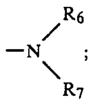 ;

$R_4$, $R_5$, $R_6$, and $R_7$, which may be the same or different from each other, each represents a hydrogen atom, a substituted or unsubstituted alkyl group, a substituted or unsubstituted aryl group, or a substituted or unsubstituted heterocyclic group, wherein the substituent for $R_3$, $R_4$, $R_5$, $R_6$, or $R_7$ is selected from an alkyl group, an aryl group, a heterocyclic group, an alkoxy group, an aryloxy group, a carboxyl group, a carbonyl group, an ester group, an amido group, a sulfamido group, an imido group, a ureido group, a sulfonyl group, a hydroxyl group, a cyano group, a nitro group, a halogen atom and a thio group; and $X_1$ represents a hydrogen atom, a halogen atom, an alkoxy group, an aryloxy group, an acyloxy group, an alkylthio group, an arylthio group, a sulfonyloxy group, an alkyloxycarbonyloxy group, an aryloxycarbonyloxy group, a carbamoylamino group, an imido group, an azo group, a sulfo group, or a thiocyanato group.

8. A color photographic silver halide light-sensitive material as in claim 1, wherein the magenta coupler residue is derived from formula (III), (IV), (V), (VI), or (XV)

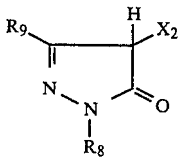

(III)

wherein $R_8$ and $R_9$ each represents a group used in usual 4-equivalent type pyrazolone couplers; and $X_2$ represents a group releasable upon an oxidative coupling reaction with a developing agent;

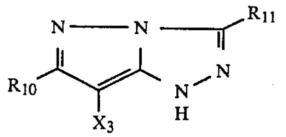

(IV)

wherein $R_{10}$ and $R_{11}$ each represents a hydrogen atom, a substituted or unsubstituted acyclic or cyclic alkyl group, a substituted or unsubstituted alkenyl group, a substituted or unsubstituted aryl group, a substituted or unsubstituted heterocyclic group, a substituted or unsubstituted amino group, a substituted or unsubstituted acylamino group, a hydroxyl group, a substituted or unsubstituted alkoxy group, a substituted or unsubstituted aryloxy group, a substituted or unsubstituted alkoxycarbonyl group, a substituted or unsubstituted aryloxycarbonyl group, a substituted or unsubstituted carbamoyl group, a substituted or unsubstituted sulfamoyl group, or a substituted or unsubstituted sulfonamido group; and $X_3$ represents a group releasable upon an oxidative coupling reaction with a developing agent;

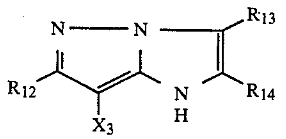

(V)

wherein $R_{12}$, $R_{13}$, and $R_{14}$ each represents a hydrogen atom, an acyclic or cyclic alkyl group, an aryl group, a heterocyclic group, a cyano group, an alkoxy group, an aryloxy group, an acylamino group, an anilino group, a ureido group, a sulfamoyl group, a sulfonamido group, a carbamoyl group, a sulfonyl group, or an alkoxycarbonyl group, or $R_{13}$ and $R_{14}$ jointly form a 5- to 7-membered ring; and $X_3$ is as defined above for formula (IV);

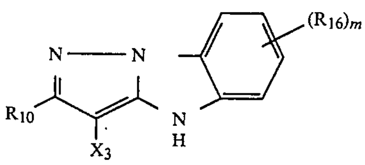

(VI)

wherein $R_{10}$ and $X_3$ are as defined above for formula (IV); $R_{16}$ represents a hydrogen atom, a substituted or unsubstituted acyclic or cyclic alkyl group, a substituted or unsubstituted alkenyl group, a substituted or unsubstituted aralkyl group, a substituted or unsubstituted aryl group, a substituted or unsubstituted heterocyclic group, a halogen atom, a substituted or unsubstituted alkoxy group, a substituted or unsubstituted aryloxy group, a cyano group, a substituted or unsubstituted acylamino group, a substituted or unsubstituted sulfonamido group, a substituted or unsubstituted carbamoyl group, a substituted or unsubstituted sulfamoyl group, a substituted or unsubstituted alkoxycarbonyl group, or a substituted or unsubstituted sulfamoylamino group; and m represents an integer of 0 to 4; and

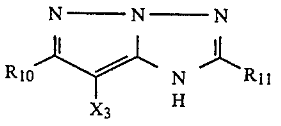

(XV)

wherein $R_{10}$, $R_{11}$, and $X_3$ are as defined above for formula (IV).

9. A color photographic silver halide light-sensitive material as in claim 7, wherein $R_8$ is a substituted or unsubstituted acyclic or cyclic alkyl group, a substituted or unsubstituted alkenyl group, a substituted or unsubstituted aryl group, or a substituted or unsubstituted heterocyclic group; $R_9$ is an anilino group, an acylamino group, or a ureido group; $X_2$ and $X_3$ each is a hydrogen atom, a halogen atom, an alkoxy group, an aryloxy group, an acyloxy group, an alkylthio group, an arylthio group, a sulfonyloxy group, an alkyloxycarbonyloxy group, an aryloxycarbonyloxy group, a carbamoylamino group, an imido group, an azo group, a sulfo group, or a thiocyanato group, wherein substituents for $R_8$, $R_{10}$, $R_{11}$, and $R_{16}$ is selected from an alkyl group, an aryl group, a heterocyclic group, an alkoxy group, an aryloxy group, a carboxyl group, a carbonyl group, an ester group, an amido group, a sulfamido group, an imido group, a ureido group, a sulfonyl group, a hydroxyl group, a cyano group, a nitro group, a halogen atom, and a thio group.

10. A color photographic silver halide light-sensitive material as in claim 1, wherein the cyan coupler residue is derived from the formula (VII)

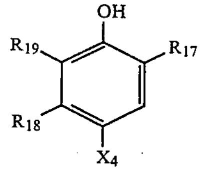

(VII)

wherein $R_{17}$ and $R_{18}$ each represents a hydrogen atom, an acyclic or cyclic alkyl group, an alkoxy group, an aryloxy group, or a group represented by formula (VIII), (IX), (X), (XI), or (XII)

—NHCO.B (VIII)

—NH—$SO_2$—B (IX)

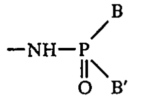
(X)

—NHCONH—B (XI)

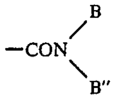
(XII)

wherein B and B′, which may be the same or different from each other, each represents an acyclic or cyclic alkyl group, an aryl group, or a heterocyclic group; and B″ represents a hydrogen atom, a substituted or unsubstituted acyclic or cyclic alkyl group, a substituted or unsubstituted aryl group, or a substituted or unsubstituted heterocyclic group; $R_{19}$ represents a hydrogen atom, an acyclic or cyclic alkyl group, an aryl group, a heterocyclic group, a halogen atom, an alkoxy group or an aryloxy group; or $R_{18}$ and $R_{19}$ jointly form a 5- or 6-membered non-metallic atom ring; and $X_4$ represents a group releasable upon an oxidative coupling reaction with a developing agent.

11. A color photographic silver halide light-sensitive material as claimed in claim 10, wherein substituents for B″ are selected from an alkyl group, an aryl group, a heterocyclic group, an alkoxy group, an aryloxy group, a carboxyl group, a carbonyl group, an ester group, an amido group, a sulfamido group, an imido group, a ureido group, a sulfonyl group, a hydroxyl group, a cyano group, a nitro group, a halogen atom, and a thio group; and $X_4$ represents a hydrogen atom, a halogen atom, an alkoxy group, an aryloxy group, an acyloxy group, an alkylthio group, an arylthio group, a sulfonyloxy group, an alkyloxycarbonyloxy group, an aryloxycarbonyloxy group, a carbamoylamino group, an imido group, an azo group, a sulfo group, or a thiocyanato group.

12. A color photographic silver halide light-sensitive material as in claim 1, wherein the group —CN and the group —O—$R_1$—CONH—A are in the relation of an ortho- or para-position.

13. A color photographic silver halide light-sensitive material as in claim 1, wherein $R_2$ is a halogen atom, an alkyl group, an acylamino group, or a sulfonamido group.

14. A color photographic silver halide light-sensitive material as in claim 1, wherein n is 0.

15. A color photographic silver halide light-sensitive material as in claim 1, wherein the coupler is represented by formula (XIII) or (XIV)

(XIII)
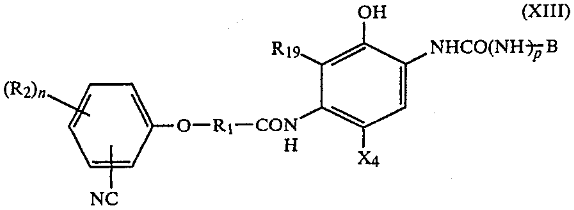

(XIV)
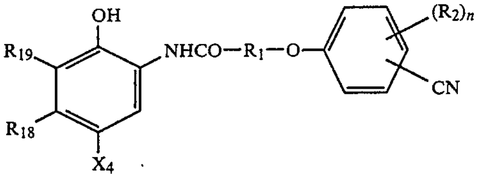

wherein $R_1$ represents a substituted or unsubstituted acyclic or cyclic alkylene group; $R_2$ represents a halogen atom, a hydroxyl group, a cyano group, a substituted or unsubstituted alkyl group, a substituted or unsubstituted acylamino group, a substituted or unsubstituted sulfonamido group, or a substituted or unsubstituted acyl group; n represents an integer of 0 to 3; $R_{18}$ represents a hydrogen atom, an acyclic or cyclic alkyl group, an alkoxy group, an aryloxy group or a group represented by formula (VIII), (IX), (X), (XI), or (XII)

—NHCO—B (VIII)
—NH—$SO_2$—B (IX)

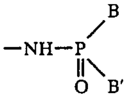
(X)

—NHCONH—B (XI)

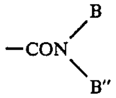
(XII)

wherein B and B′, which may be the same or different from each other, each represents an acyclic or cyclic alkyl group, an aryl group or a heterocyclic group; and B″ represents a hydrogen atom, a substituted or unsubstituted aryl group, or a substituted or unsubstituted heterocyclic group; $R_{19}$ represents a hydrogen atom, an acyclic or cyclic alkyl group, an aryl group, a heterocyclic group, a halogen atom, an alkoxy group, or an aryloxy group; or $R_{18}$ and $R_{19}$ jointly form a 5- or 6-membered non-metallic atom ring; B is as defined above; and p represents 0 or 1, wherein substituents for $R_1$, $R_2$, or B″ are selected from an alkyl group, an aryl group, a heterocyclic group, an alkoxy group, an aryloxy group, a carboxyl group, a carbonyl group, an ester group, an amido group, a sulfamido group, an imido group, a ureido group, a sulfonyl group, a hydroxyl group, a cyano group, a nitro group, a halogen atom, and a thio group.

16. A color photographic silver halide light-sensitive material as in claim 15, wherein in formula (XIII) $R_{19}$ is a hydrogen atom, B is an aryl group, and p is 0.

17. A color photographic silver halide light-sensitive material as in claim 15, wherein in formula (XIV) $R_{19}$ is a hydrogen atom, or $R_{19}$ and $R_{18}$ jointly form a 5- or 6-membered non-metallic atom ring.

18. A color photographic silver halide light-sensitive material as in claim 17, wherein said non-metallic atom ring contains at least one nitrogen atom.

* * * * *